(12) United States Patent
Xu et al.

(10) Patent No.: US 11,903,571 B2
(45) Date of Patent: Feb. 20, 2024

(54) FLEXIBLE SURGICAL INSTRUMENT SYSTEM WITH PREPOSITIONED DRIVE INPUT

(71) Applicant: Beijing Surgerii Robotics Company Limited, Beijing (CN)

(72) Inventors: Kai Xu, Beijing (CN); Shu'an Zhang, Beijing (CN); Zhengchen Dai, Beijing (CN); Jiangran Zhao, Beijing (CN); Huan Liu, Beijing (CN); Yuyang Chen, Beijing (CN); Zhixiong Yang, Beijing (CN); Zhijun Zhu, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 1123 days.

(21) Appl. No.: 16/329,723

(22) PCT Filed: Aug. 30, 2017

(86) PCT No.: PCT/CN2017/099754
§ 371 (c)(1),
(2) Date: Feb. 28, 2019

(87) PCT Pub. No.: WO2018/041158
PCT Pub. Date: Mar. 8, 2018

(65) Prior Publication Data
US 2019/0231329 A1    Aug. 1, 2019

(30) Foreign Application Priority Data

Aug. 31, 2016    (CN) .......................... 201610796071.6
Aug. 31, 2016    (CN) ......................... 201610798138.X (51) Int. Cl.
A61B 17/00 (2006.01)
A61B 34/30 (2016.01)
A61B 17/29 (2006.01)

(52) U.S. Cl.
CPC ........ A61B 17/00234 (2013.01); A61B 17/00 (2013.01); A61B 34/30 (2016.02);
(Continued)

(58) Field of Classification Search
CPC ... A61B 17/00234; A61B 17/00; A61B 17/29; A61B 34/30; A61B 34/71;
(Continued)

(56) References Cited

U.S. PATENT DOCUMENTS

2003/0149338 A1    8/2003    Francois et al.
2011/0028991 A1    2/2011    Ikeda et al.
(Continued)

FOREIGN PATENT DOCUMENTS

CN    101653353 A    2/2010
CN    103025225 A    4/2013
(Continued)

OTHER PUBLICATIONS

Ding, J. et al., "Design and Coordination Kinematics of an Insertable Robotic Effectors Platform for Single-Port Access Surgery," IEEE/ASME Transactions on Mechatronics, vol. 18, No. 5, Oct. 2013, 13 pages.
(Continued)

*Primary Examiner* — Brooke Labranche
(74) *Attorney, Agent, or Firm* — McCoy Russell LLP (57) ABSTRACT

Disclosed is a flexible surgical instrument system, comprising: a distal structural body comprising at least one distal structural segment, the at least one distal structural segment comprising a distal fixing disk and distal structural backbones; a proximal structural body comprising at least one
(Continued)

proximal structural segment, the at least one proximal structural segment comprising a proximal fixing disk, proximal structural backbones, and driving backbones, the distal structural backbones being securely connected in one-to-one correspondence to or the same as corresponding proximal structural backbones, and a driving unit comprising a linear motion mechanism operable to convert a first rotary motion into linear motions to cooperatively push or pull a pair of driving backbones of the driving backbones to turn the at least one proximal structural segment.

16 Claims, 11 Drawing Sheets

(52) U.S. Cl.
CPC ............ *A61B 2017/00314* (2013.01); *A61B 2017/00323* (2013.01); *A61B 2017/00336* (2013.01); *A61B 2017/2932* (2013.01); *A61B 2034/301* (2016.02)

(58) Field of Classification Search
CPC .......... A61B 2017/00314; A61B 2017/00323; A61B 2017/00336; A61B 2017/2932; A61B 2017/00292; A61B 2017/003; A61B 2017/00318; A61B 2034/301
See application file for complete search history.

(56) References Cited

U.S. PATENT DOCUMENTS

| | | | |
|---|---|---|---|
| 2013/0131695 A1 | 5/2013 | Scarfogliero et al. | |
| 2016/0016319 A1 | 1/2016 | Remirez et al. | |
| 2016/0135914 A1* | 5/2016 | Isoda | A61B 34/72 606/130 |

FOREIGN PATENT DOCUMENTS

| | | | |
|---|---|---|---|
| CN | 103085083 | A | 5/2013 |
| CN | 103315781 | A | 9/2013 |
| CN | 103340707 | A | 10/2013 |
| CN | 103340731 | A | 10/2013 |
| CN | 103707322 | A | 4/2014 |
| CN | 103948435 | A | 7/2014 |
| CN | 103707322 | B | 4/2016 |
| CN | 105856213 | A | 8/2016 |
| CN | 106308935 | A | 1/2017 |
| CN | 106420059 | A | 2/2017 |
| EP | 1274480 | B1 | 7/2006 |
| EP | 2777595 | A2 | 9/2014 |
| WO | 2009094670 | A1 | 7/2009 |
| WO | 2013158978 | A1 | 10/2013 |

OTHER PUBLICATIONS

Xu, K. et al., "Design of a Hyper-Redundant Continuum Manipulator for Intra-Cavity Tasks," Proceedings of the 2014 IEEE International Conference on Robotics and Biomimetics, Dec. 5, 2014, Bali, Indonesia, 6 pages.
Xu, K. et al., "Development of the SJTU Unfoldable Robotic System (SURS) for Single Port Laparoscopy," IEEE/ASME Transactions on Mechatronics, vol. 20, No. 5, Oct. 2015, Available as Early as Nov. 11, 2014, 13 pages.
State Intellectual Property Office of the People's Republic of China, Office Action and Search Report Issued in Application No. 201610796071.6, dated Jun. 21, 2018, 7 pages.
State Intellectual Property Office of the People's Republic of China, Office Action and Search Report Issued in Application No. 201610798138.X, dated Jul. 3, 2018, 11 pages.
European Patent Office, Supplementary European Search Report Issued in Application No. 17845460.9, dated Mar. 11, 2020, Germany, 3 pages.
ISA State Intellectual Property Office of the People's Republic of China, International Search Report Issued in Application No. PCT/CN2017/099754, dated Dec. 4, 2017, WIPO, 6 pages.

* cited by examiner

FLEXIBLE SURGICAL INSTRUMENT SYSTEM WITH PREPOSITIONED DRIVE INPUT

CROSS REFERENCE TO RELATED APPLICATIONS

The present patent application is a U.S. national phase of Chinese International Application No. PCT/CN2017/099754 entitled "FLEXIBLE SURGICAL INSTRUMENT SYSTEM WITH PREPOSITIONED DRIVE INPUT" and filed on Aug. 30, 2017. Chinese International Application No. PCT/CN2017/099754 claims the priorities priority to Chinese Patent Application No. 201610798138.X filed on Aug. 31, 2016, and Chinese Patent Application No. 201610796071.6 filed on Aug. 31, 2016. The entire contents of each of the above-identified applications are incorporated herein by reference for all purposes.

TECHNICAL FIELD

The present invention relates to a flexible surgical instrument system with a prepositioned drive input, belonging to the field of medical instruments.

BACKGROUND ART

Multi-port laparoscopic minimally invasive surgery has occupied an important position in surgery because of its small incision and rapid postoperative recovery. The existing da Vinci surgical robot of the Intuitive Surgical, Inc. assists doctors in completing the multi-port laparoscopic minimally invasive surgery and has achieved great commercial success.

For the minimally invasive surgery, after the multi-port laparoscopic surgery, single-port laparoscopic surgery and natural orifice transluminal noninvasive surgery have been developed, which have less trauma to the patient and higher postoperative outcomes. However, in the single-port laparoscopic surgery and the natural orifice transluminal noninvasive surgery, all surgical instruments including a visual illumination module and a surgical manipulator have access to the surgical site through a single channel, which is extremely stringent for the preparation of the surgical instruments. A distal structure of the existing surgical instrument mainly consists of multiple rods articulated in series, and is driven by a pulling force from a steel wire rope, so that the surgical instrument can turn at a hinge joint. Since the steel wire rope has to be continuously tensioned by a pulley, this driving method has difficulty in further miniaturizing the surgical instrument, and also has difficulty in further improving the moving performance of the instrument.

Although the Intuitive Surgical, Inc. has recently introduced a da Vinci Single-Site surgical robot, in which the original rigid surgical instrument is modified into a semi-rigid surgical instrument and a pre-bent sleeve is additionally provided so as to improve the moving performance of the surgical instrument to a certain extent, it still cannot fundamentally solve the problems faced by the traditional microsurgical instruments.

SUMMARY OF INVENTION

In view of the above problems, an object of the present invention is to provide a flexible surgical instrument system with a prepositioned drive input, which can be better applied to a surgical robot system that passes through a natural orifice of human body or a single surgical incision and performs an operation.

In order to achieve the above object, the following technical solution is used in the invention: a flexible surgical instrument system with a prepositioned drive input, the flexible surgical instrument system comprising a flexible continuous body structure and a driving unit, wherein the flexible continuous body structure comprises a distal structural body, a proximal structural body and a middle connecting body; the distal structural body comprises at least one distal structural segment, and the distal structural segment comprises distal spacing disks, a distal fixing disk and structural backbones; the proximal structural body comprises proximal structural segments having the same number as the number of distal structural segments, and the proximal structural segment comprises proximal spacing disks, a proximal fixing disk and structural backbones; the middle connecting body comprises two channel fixing plates and a structural backbone guide channel provided between the two channel fixing plates; the structural backbones of the distal structural segment are securely connected, in one-to-one correspondence, to or are the same as the structural backbones of the proximal structural segment, one end of each of the structural backbones is securely connected to the proximal fixing disk, passing through the proximal spacing disks, the structural backbone guide channel and the distal spacing disks in sequence, the other end of the structural backbone is securely connected to the distal fixing disk; and the driving unit comprises a driving unit fixing plate arranged in front of the middle connecting body, a plurality of linear motion mechanisms for converting a rotary motion input into a linear motion output are provided between the driving unit fixing plate and the channel fixing plate, output ends of the linear motion mechanisms are connected to one end of a driving backbone, the driving backbone passes through the proximal spacing disks, and the other end of the driving backbone is securely connected to the proximal fixing disk.

Preferably, the number of the proximal structural segments is equal to the number of the distal structural segments.

In one preferred embodiment, the linear motion mechanism comprises a threaded rod rotatably arranged between the driving unit fixing plate and the channel fixing plate, a shaft securely arranged between the driving unit fixing plate and the channel fixing plate, and a slider slidably connected to the shaft and threadedly fitted with the threaded rod; and the driving backbone is securely connected to the slider.

In one preferred embodiment, the threaded rods pass through the driving unit fixing plate, a gear is securely connected to the threaded rod at a front side of the driving unit fixing plate, every two of the threaded rods being a group; a pair of the driving backbones are securely connected to the slider on one group of the threaded rods; and the gears on one group of the threaded rods meshes with each other, and a male coupling directly or indirectly connected to an output shaft of a motor is securely connected to a front end of one of the threaded rods in one group of the threaded rods.

In one preferred embodiment, the linear motion mechanism comprises double-head threaded rods rotatably arranged between the driving unit fixing plate and the channel fixing plate, and shafts securely arranged between the driving unit fixing plate and the channel fixing plate, and two threaded sections of the double-head threaded rod are respectively connected to a slider by a threaded fit, each of the sliders being slidably connected to one of the shafts; a pair of the driving backbones are respectively securely connected to the two sliders located on the same double-head threaded rod; and the double-head threaded rod passes through the driving unit fixing plate, and a front end of the double-head threaded rod is securely connected to a male coupling directly or indirectly connected to an output shaft of a motor.

In one preferred embodiment, a driving backbone guide channel is provided between the two channel fixing plates, and the driving backbone passes through the driving backbone guide channel.

In one preferred embodiment, when the distal structural body comprises two or more distal structural segments, the structural backbones on the distal structural segment away from the middle connecting body pass through the distal fixing disk and the distal spacing disks on the distal structural segment near the middle connecting body, or pass through the interior of the structural backbones on the distal structural segment near the middle connecting body; and when the proximal structural body comprises two or more proximal structural segments, the structural backbones on the proximal structural segment away from the middle connecting body pass through the proximal fixing disk and the proximal spacing disks on the proximal structural segment near the middle connecting body, or pass through the interior of the structural backbones on the proximal structural segment near the middle connecting body.

In one preferred embodiment, the distal structural body is externally covered with an envelope, a front end of the envelope is securely connected to a surgical end effector, and a rear end of the envelope is connected to a rotary driving mechanism in the driving unit.

In one preferred embodiment, the rotary driving mechanism comprises a rotary sleeve rotatably supported at a front side of the driving unit fixing plate, and a front end of the rotary sleeve is securely connected to the envelope; and the front side of the driving unit fixing plate is further provided with a rotary shaft, a pair of gears meshing with each other are provided on the rotary shaft and the rotary sleeve, and a male coupling directly or indirectly connected to an output shaft of a motor is securely connected to a front end of the rotary shaft.

In one preferred embodiment, a front end of the distal structural body is provided with a surgical end effector, a actuation wire of the surgical end effector passes through the distal structural body, and the other end of the actuation wire is connected to a surgical end effector driving mechanism which is located on the channel fixing plate and is used for converting a rotary motion input into a linear motion output.

In one preferred embodiment, the surgical end effector driving mechanism comprises a base securely connected to the channel fixing plate, a connecting rod is rotatably connected to the base, one end of the connecting rod is connected to a first slider, the first slider is slidably connected to a first shaft arranged on the base, and the actuation wire of the surgical end effector is securely connected to the first slider; the other end of the connecting rod is connected to a second slider, and the second slider is slidably connected to a second shaft arranged on the channel fixing plate; and a driving threaded rod is rotatably supported on the driving unit fixing plate, a front end of the driving threaded rod is provided with a male coupling directly or indirectly connected to an output shaft of a motor, a third slider is connected to the driving threaded rod by a threaded fit, the third slider is slidably connected to a third shaft arranged between the driving unit fixing plate and the channel fixing plate, and the third slider is connected to the second slider by means of a driving rod.

In one preferred embodiment, the flexible surgical instrument system further comprises a shell, a sterile barrier, a motor assembly and a linear module, wherein the driving unit fixing plate and the channel fixing plates are all securely connected to the shell, and the proximal structural body, the middle connecting body and the driving unit are all located inside the shell; a front end of the shell is connected to the motor assembly by means of the sterile barrier; and the linear module comprises a support, a motor securely connected to the support, and a linear feed mechanism securely connected to an output shaft of the motor, an output end of the linear feed mechanism is securely connected to a housing of the motor assembly, and the motor drives the motor assembly by means of the linear feed mechanism to drive the flexible continuous body structure and the driving unit to perform a linear motion by means of the sterile barrier.

In one preferred embodiment, the linear feed mechanism comprises a lead screw rotatably connected to the support, the lead screw is sheathed with a slider which is threadedly fitted with the lead screw, a linear sliding groove is provided on the support, and the slider is slidably arranged in the linear sliding groove; and an output shaft of the motor is securely connected to the lead screw by means of a coupling.

In one preferred embodiment, the flexible surgical instrument system further comprises a shell, wherein the driving unit fixing plate and the channel fixing plates are all securely connected to the shell, the proximal structural body, the middle connecting body and the driving unit are all located inside the shell, a front end of the shell is connected to a motor assembly by means of a sterile barrier, the sterile barrier comprises a cover and a female coupling rotatably arranged on the cover, a rear end of the female coupling is connected to the male coupling, a front end of the female coupling is connected to a motor output shaft of the motor assembly by means of another male coupling, and the periphery of the cover is connected to a sterile membrane.

The present invention has the following advantages by utilizing the above technical solutions: 1. In the present invention, a flexible continuous body structure comprising a proximal structural body, a middle connecting body and a distal structural body is used as the main body and cooperates with a driving unit, wherein the distal structural body is linked to the proximal structural body by means of the middle connecting body, the driving unit is linked to the proximal structural body, and when the driving unit drives the proximal structural body to turn in any direction, the distal structural body correspondingly turns in the opposite direction, and thus the flexible surgical arm formed by the distal structural body and an envelope is capable of turning in any direction. 2. In the present invention, the distal structural body is externally covered with an envelope, a rear end of the envelope is connected to a mechanism for driving the envelope to rotate, and a front end of the envelope is connected to a surgical end effector, and thus the angle of the surgical end effector can be adjusted by means of driving the envelope to rotate. 3. In the present invention, a actuation wire of the surgical end effector passes through the distal structural body and reaches the middle connecting body, and a surgical end effector driving mechanism for driving the actuation wire to move in a linear motion is provided at the position of the middle connecting body, thus implementing the motion control for the surgical end effector. 4. In the present invention, since the shell is connected to a motor assembly by means of a sterile barrier, the unsterilized motor assembly is effectively separated from other sterilized parts, thus ensuring the practicability of clinical surgery. 5. In the present invention, a linear module is further provided, and the linear module is connected to a housing part of the motor assembly and can drive the motor assembly, the sterile barrier and the shell to move in a linear motion, and thus the flexible surgical arm also has a linear feed degree of freedom.

The present invention can be applied to the single-port endoscopic surgery, and can also be applied to the natural orifice transluminal non-invasive surgery.

DETAILED DESCRIPTION OF THE EMBODIMENTS

The present invention is described in detail below in conjunction with the accompanying drawings and embodiments.

Figure 1:
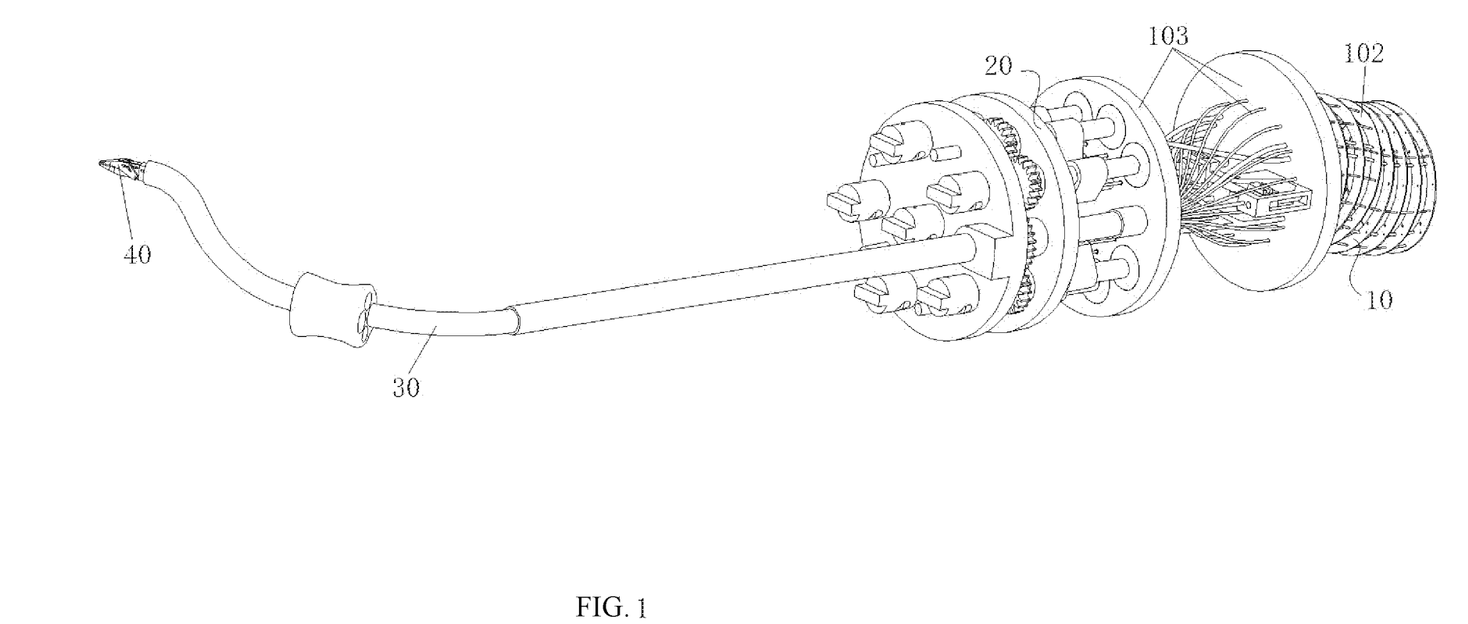
FIG. 1 is an overall structural schematic diagram according to the present invention.

As shown in FIG. 1, the present invention comprises a flexible continuous body structure 10 and a driving unit 20.

Figure 2:
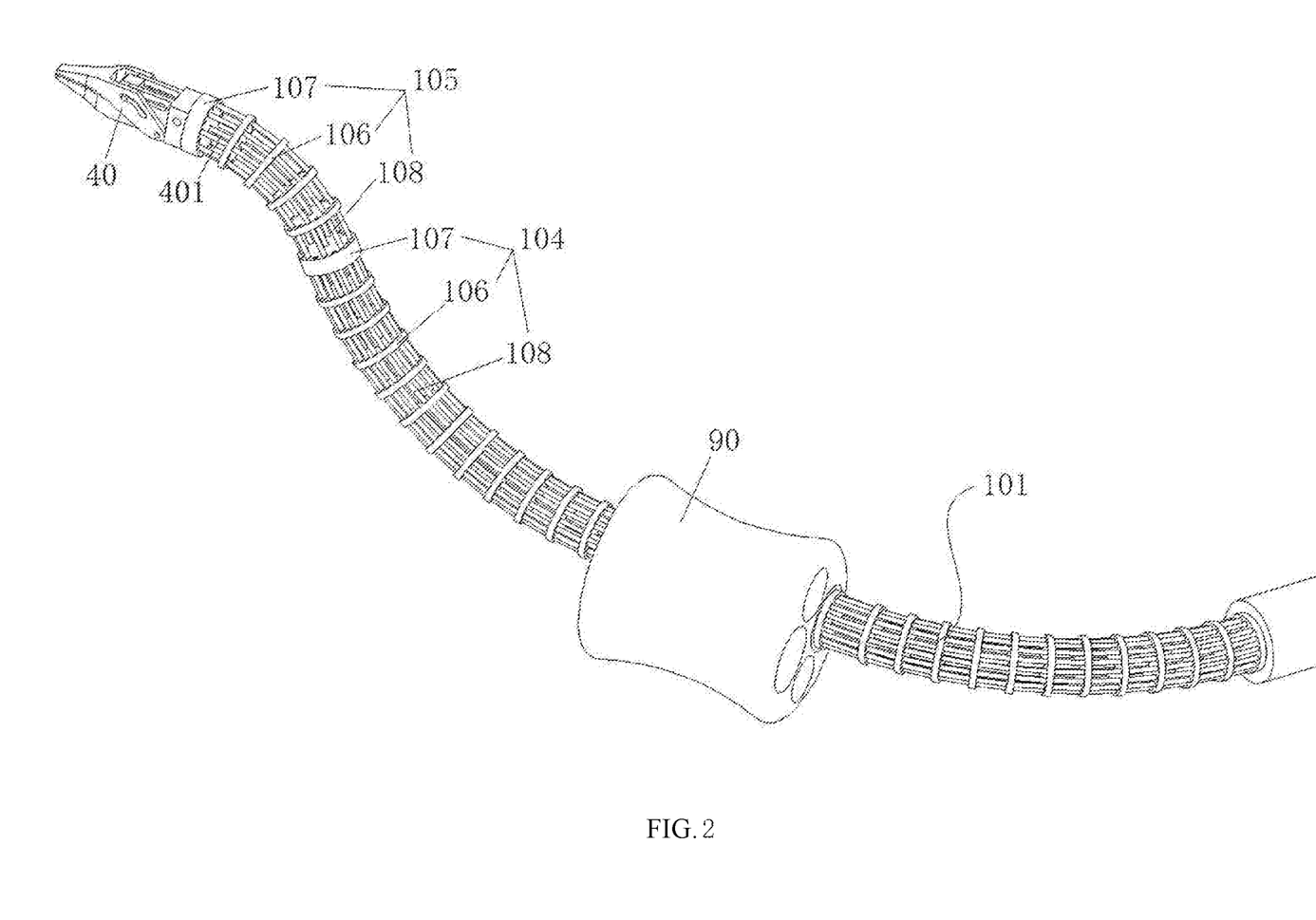
FIG. 2 is a structural schematic diagram of a distal structural body according to the present invention.
Figure 3:
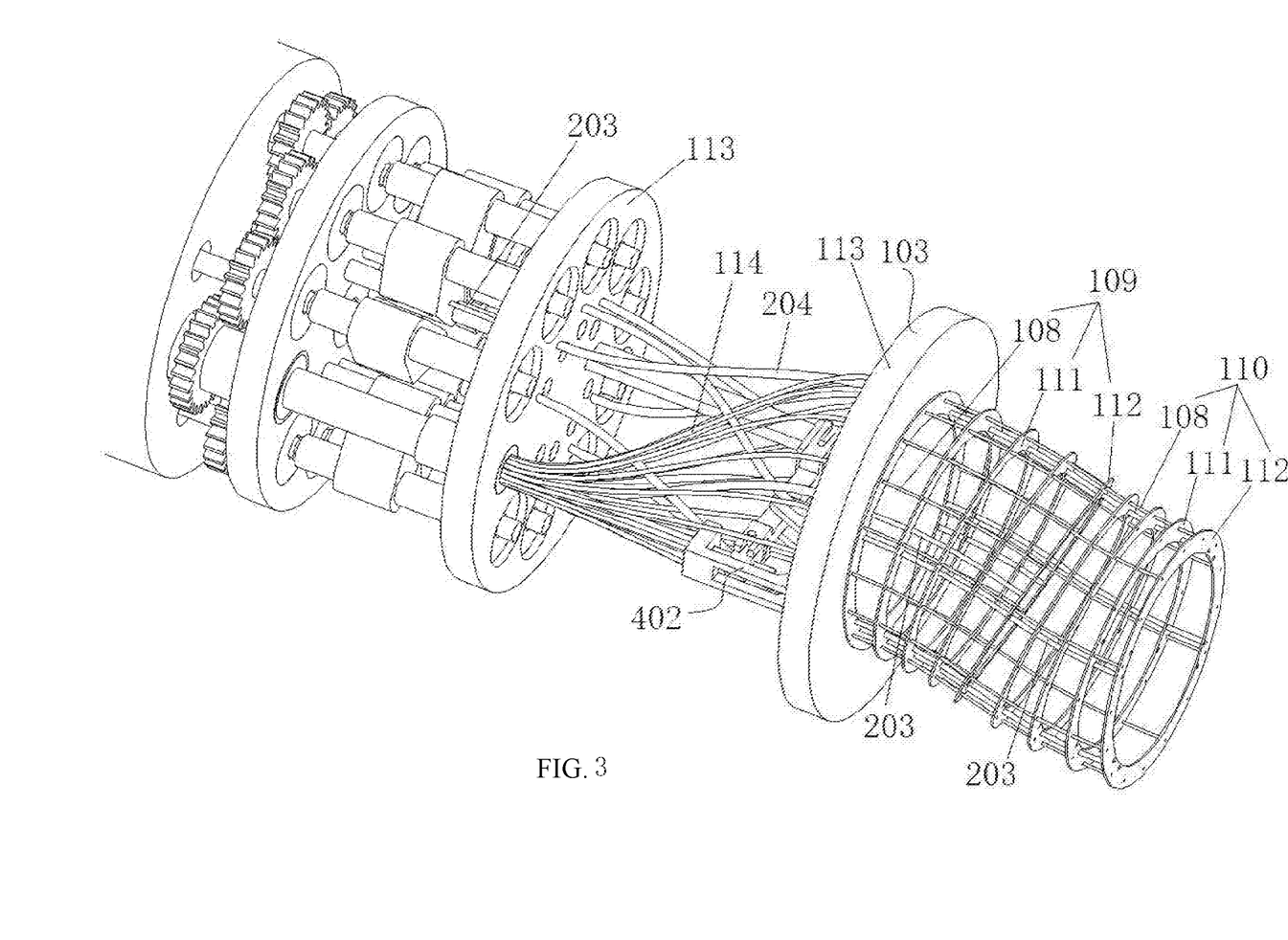
FIG. 3 is a structural schematic diagram of a proximal structural body and a middle connecting body according to the present invention.

The flexible continuous body structure 10 of the present invention comprises a distal structural body 101 (as shown in FIG. 2), a proximal structural body 102 and a middle connecting body 103, wherein the distal structural body 101 is linked to the proximal structural body 102 by means of the middle connecting body 103; and the driving unit 20 is linked to the proximal structural body 102, and when the driving unit 20 drives the proximal structural body 102 to turn in any direction, the distal structural body 101 correspondingly turns in the opposite direction. As shown in FIG. 2, the distal structural body 101 comprises two distal structural segments 104, 105, and each of the distal structural segments 104, 105 comprises distal spacing disks 106, a distal fixing disk 107 and structural backbones 108. The distal spacing disks 106 are uniformly distributed in the distal structural body 101 at intervals, and have a function to prevent the structural backbones 108 from becoming unstable when being pushed. As shown in FIG. 3, the proximal structural body 102 comprises two proximal structural segments 109, 110, and each of the proximal structural segments 109, 110 comprises proximal spacing disks 111, a proximal fixing disk 112 and structural backbones 108. The proximal spacing disks 111 are uniformly distributed in the proximal structural body 102 at intervals, and have a function to prevent the structural backbones 108 from becoming unstable when being pushed. The structural backbones 108 on the first proximal structural segment 109 are securely connected, in one-to-one correspondence, to or are the same as the structural backbones 108 on the first distal structural segment 104, and the structural backbones 108 on the second proximal structural segment 110 are securely connected, in one-to-one correspondence, to or are the same as the structural backbones 108 on the second distal structural segment 105; and for each of the distal structural segments 104, 105 or the proximal structural segments 109, 110, the number of the structural backbones 108 is three or more. The number of the distal structural segments comprised in the distal structural body 101 and the number of the proximal structural segments comprised in the proximal structural body 102 may also be one or more than two, but the number of the proximal structural segments is always consistent with the number of the distal structural segments. The middle connecting body 103 comprises two channel fixing plates 113 and a structural backbone guide channel 114 provided between the channel fixing plates 113. One end of each of the structural backbones 108 on the first proximal structural segment 109 is securely connected to the proximal fixing disk 112 on the first proximal structural segment 109 and passes through the proximal spacing disks 111 on the first proximal structural segment 109, the structural backbone guide channel 114, and the distal spacing disks 106 on the first distal structural segment 104 in sequence, and the other end of the structural backbone is securely connected to the distal fixing disk 107 on the first distal structural segment 104. One end of each of the structural backbones 108 on the second proximal structural segment 110 is securely connected to the proximal fixing disk 112 on the second proximal structural segment 110 and passes through the proximal spacing disks 111 on the second proximal structural segment 110, the proximal fixing disk 112 on the first proximal structural segment 109, the proximal spacing disks 111 on the first proximal structural segment 109, the structural backbone guide channel 114, the distal spacing disks 106 on the first distal structural segment 104, the fixing disk 107 on the first distal structural segment 104, and the distal spacing disks 106 on the second distal structural segment 105 in sequence, and the other end of the structural backbone is securely connected to the distal fixing disk 107 on the second distal structural segment 105. The structural backbone guide channel 114 has a function to keep the shape of the structural backbones 108 unchanged under a pushing or pulling force, and the structural backbone guide channel may be of the sleeve structure as shown in FIG. 3, or may be in any other structural form, such as a multi-cavity structure, capable of maintaining the shape of the structural backbones 108 unchanged under a pushing or pulling force.

The structural backbones 108 on the first distal structural segment 104, the structural backbones 108 on the second distal structural segment 105, the structural backbones 108 on the first proximal structural segment 109, and the structural backbones 108 of the second proximal structural segment 110 are elastic elongated rods or elastic elongated tubes. When the structural backbones 108 on the first distal structural segment 104 and the structural backbones 108 on the first proximal structural segment 109 are elastic elongated tubes, the structural backbones 108 on the second distal structural segment 105 may also pass through the structural backbones 108 on the first distal structural segment 104, and accordingly the structural backbones 108 on the second proximal structural segment 110 may also pass through the interior of the structural backbones 108 of the first proximal structural segment 109.

Figure 4:
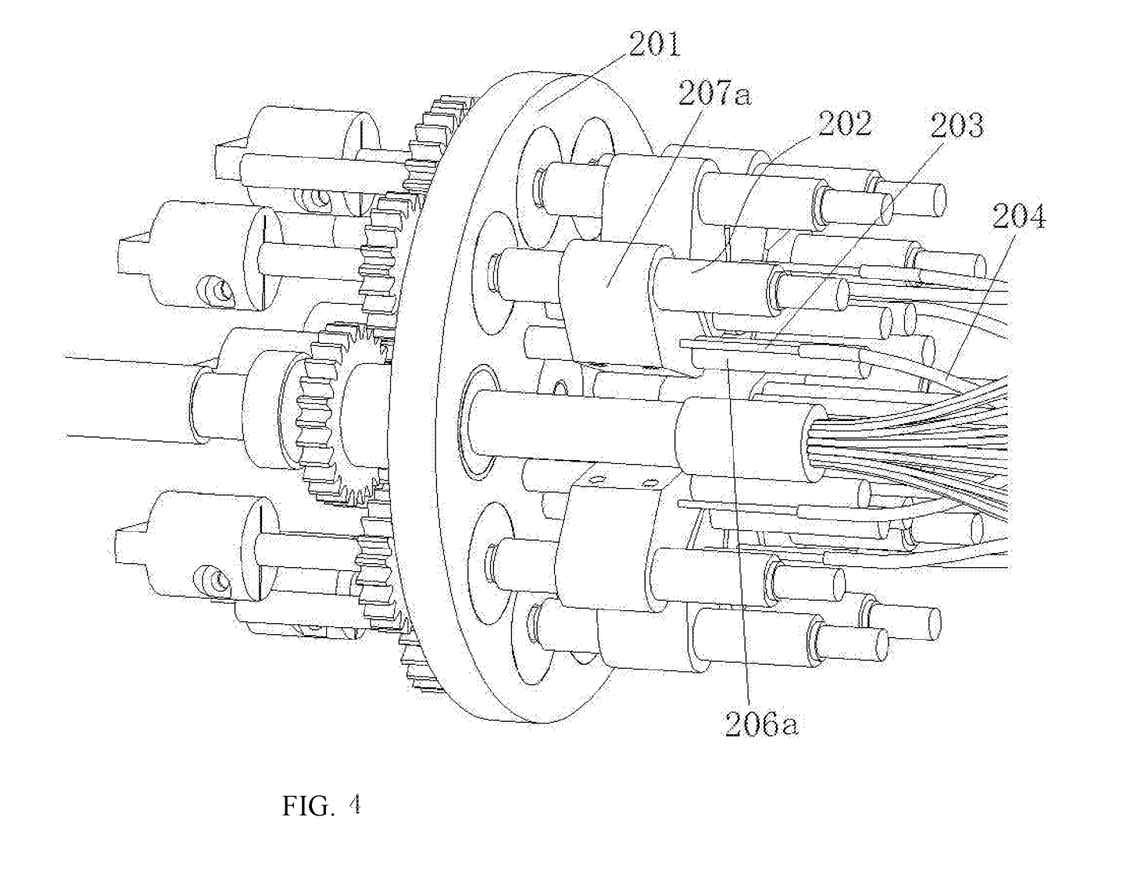
FIG. 4 is a structural schematic diagram of a driving unit using a first type of linear motion mechanism according to the present invention.

As shown in FIG. 4, the driving unit 20 comprises a driving unit fixing plate 201 arranged in front of the middle connecting body 103, a plurality of linear motion mechanisms 202 for converting a rotary motion input into a linear motion output are provided between the driving unit fixing plate 201 and the channel fixing plate 113, an output end of the linear motion mechanism 202 is securely connected to one end of a driving backbone 203, and a driving backbone guide channel 204 is further provided between the two channel fixing plates 113; and the driving backbone 203 passes through the driving backbone guide channel 204 and the proximal spacing disks 111 in sequence, and the other end of the driving backbone is securely connected to the proximal fixing disk 112. The driving backbone guide channel 204 has a function to keep the shape of the driving backbone 203 unchanged under a pushing or pulling force, and the driving backbone guide channel may be of the sleeve structure as shown in FIG. 3, or may be in any other structural form, such as a multi-cavity structure, capable of maintaining the shape of the driving backbone 203 unchanged under a pushing or pulling force. In this embodiment, eight driving backbones 203 are provided, four of which are securely connected to the proximal fixing disk 112 on the first proximal structural segment 109, and the other four are securely connected to the proximal fixing disk 112 on the second proximal structural segment 110. By means of the cooperative pushing or pulling, by the driving unit 20, of the driving backbones 203 connected to the first proximal structural segment 109, the first proximal structural segment 109 can turn at a degree of freedom in any direction, and when the first proximal structural segment 109 turns in a certain direction, the first distal structural segment 104 will turn in the opposite direction in a certain proportional relationship (determined jointly by the distribution radii of the structural backbones 108 in the first proximal structural segment 109 and in the first distal structural segment 104). Similarly, by means of the cooperative pushing or pulling, by the driving unit 20, of the driving backbones 203 connected to the second proximal structural segment 110, the second proximal structural segment 110 can turn at a degree of freedom in any direction, and when the second proximal structural segment 110 turns in a certain direction, the second distal structural segment 105 will turn in the opposite direction in a certain proportional relationship (determined jointly by the distribution radii of the structural backbones 108 of the second proximal structural segment 110 and the second distal structural segment 105). For each of the proximal structural segments 109, 110, the number of the driving backbones 203 is three or more.

Figure 5:
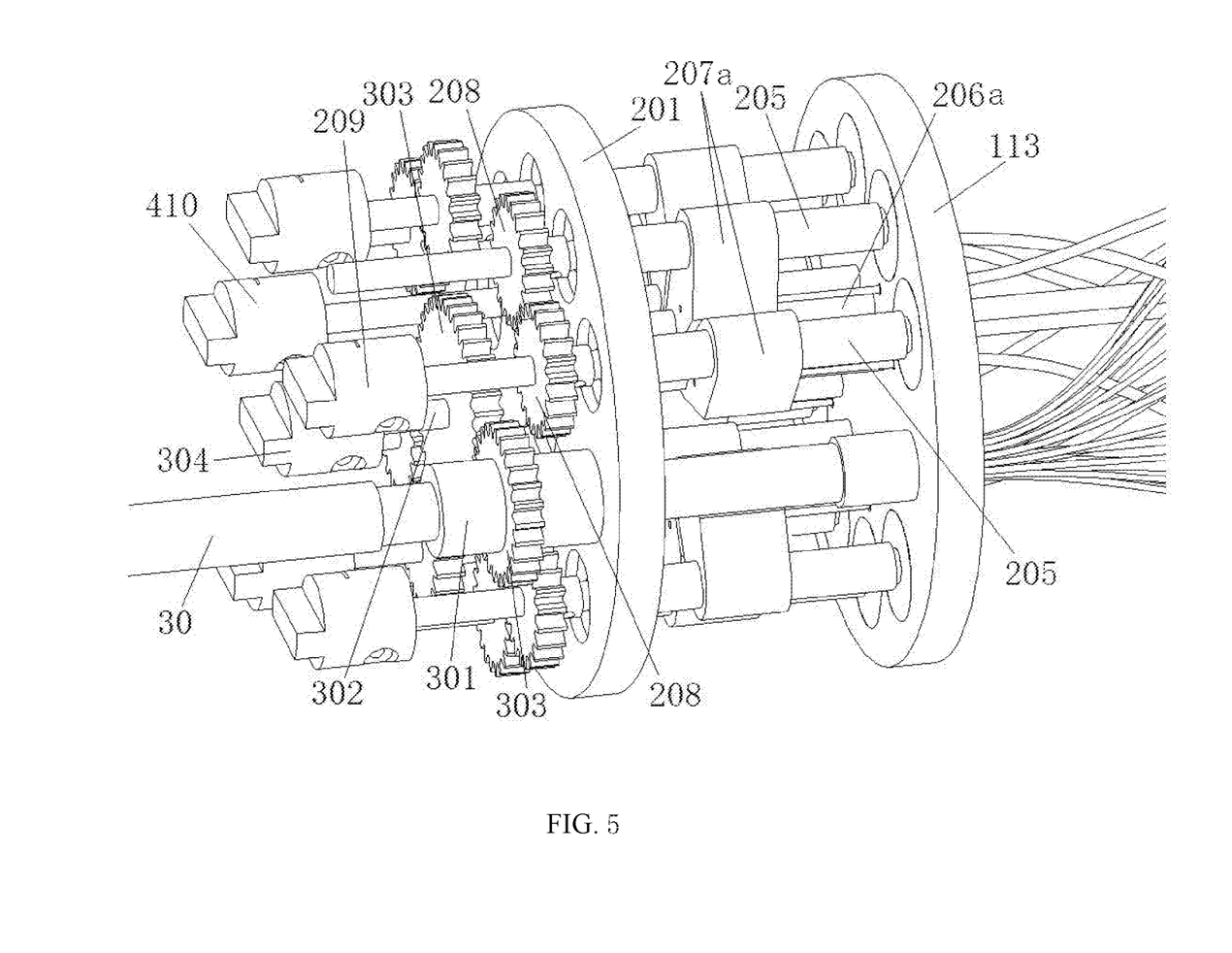
FIG. 5 is a structural schematic diagram of the driving unit in FIG. 4 viewed from another view angle.

In the above embodiment, as shown in FIGS. 4 and 5, the linear motion mechanism 202 comprises a threaded rod 205 rotatably arranged between the driving unit fixing plate 201 and the channel fixing plate 113, a shaft 206a securely arranged between the driving unit fixing plate 201 and the channel fixing plate 113, and a slider 207a slidably connected to the shaft 206a and threadedly fitted with the threaded rod 205, and the slider 207a serves as a motion end of the linear motion mechanism 202 and is securely connected to the driving backbone 203. The threaded rods 205 pass through the driving unit fixing plate 201, a gear 208 is securely connected to the threaded rod 205 at a front side of the driving unit fixing plate 201, every two of the threaded rods 205 are one group, two gears 208 located on one group of threaded rods 205 mesh with each other, and two sliders 207a on one group of the threaded rods 205 are securely connected to a pair of driving backbones 203, so as to cooperatively push or pull the pair of driving backbones 203 to implement turning of a certain structural segment in the proximal structural body 102. A male coupling 209 is securely connected to a front end of one of the threaded rods 205 in each group of the threaded rods 205. In this embodiment, four groups of, i.e., eight threaded rods 205 are provided for driving the eight driving backbones 203 to perform cooperative pushing or pulling, and accordingly four male couplings 209 are provided.

Figure 6:
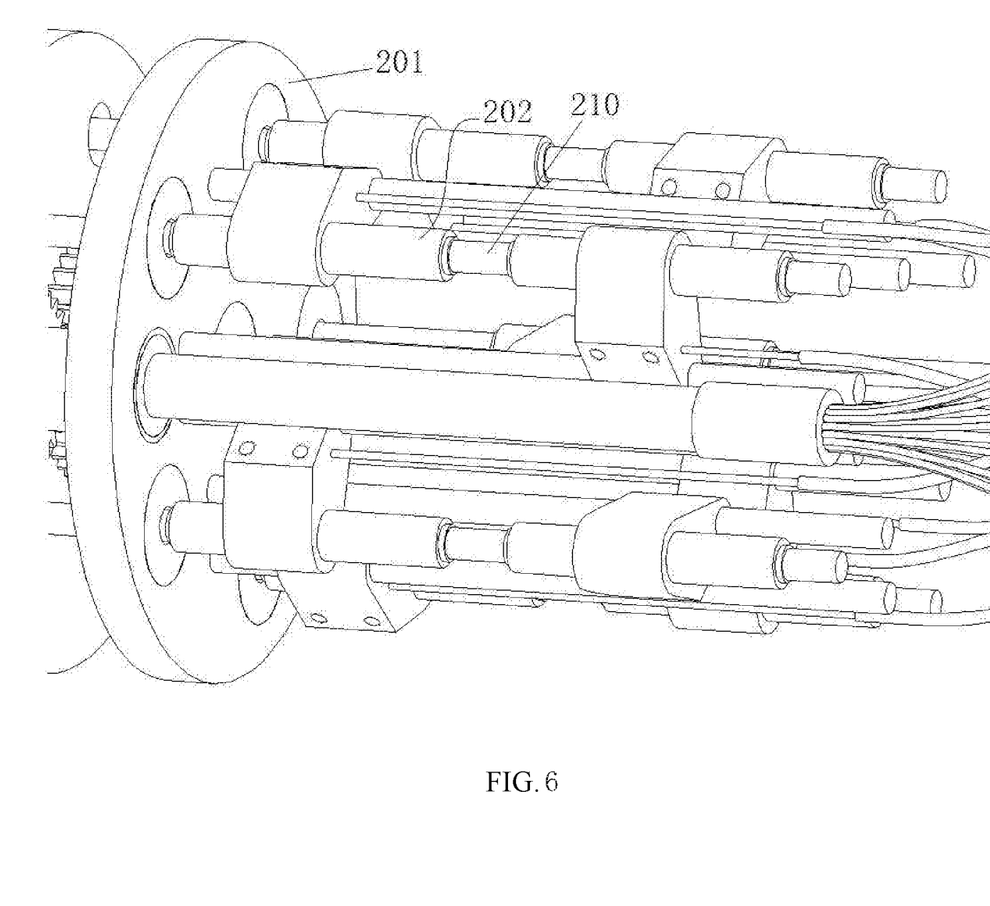
FIG. 6 is a structural schematic diagram of a driving unit using a second type of linear motion mechanism according to the present invention.
Figure 7:
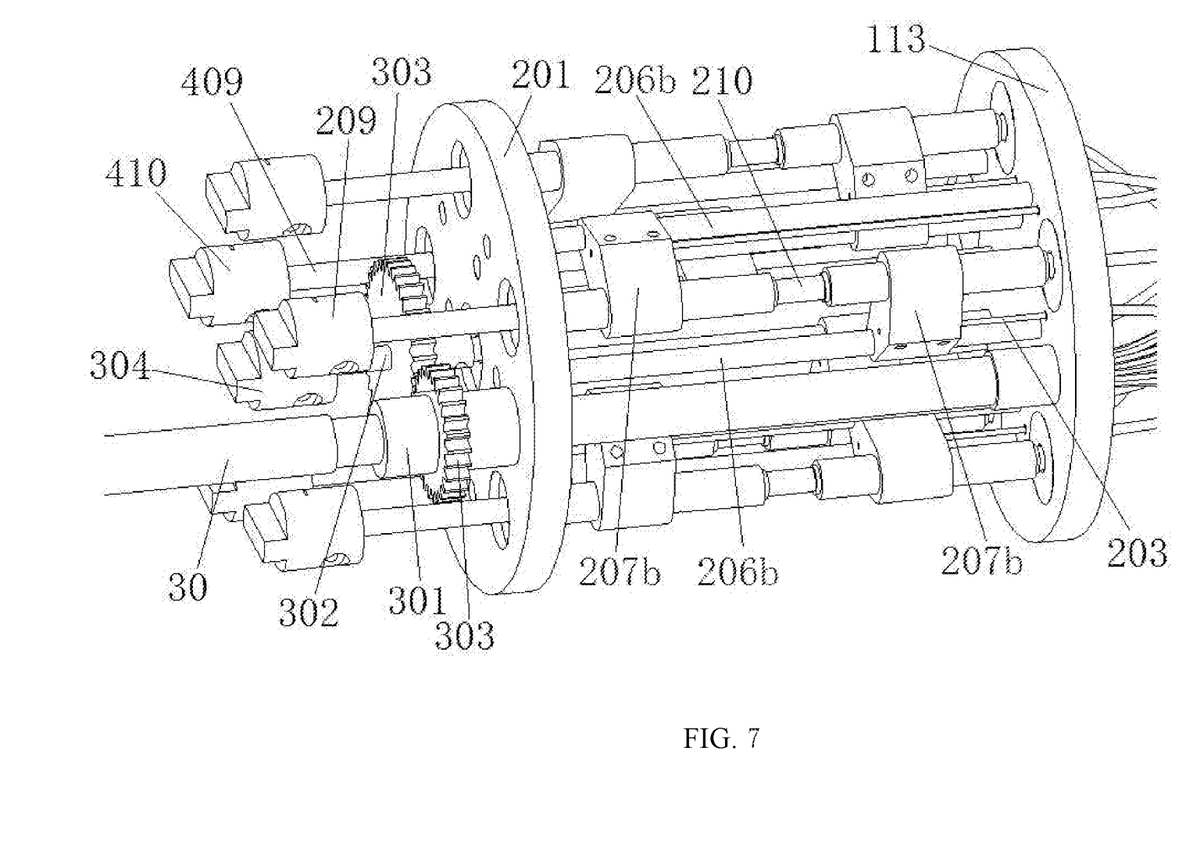
FIG. 7 is a structural schematic diagram of the driving unit in FIG. 6 viewed from another view angle.

As shown in FIGS. 6 and 7, the linear motion mechanism 202 may also be of another structure, comprising a double-head threaded rod 210 rotatably arranged between the driving unit fixing plate 201 and the channel fixing plate 113 and a shaft 206b securely arranged between the driving unit fixing plate 201 and the channel fixing plate 113, two threaded sections of the double-head threaded rod 210 are respectively connected to one of the sliders 207b by a threaded fit, and each of the sliders 207b is slidably connected to one of the shafts 206b. A pair of the driving backbones 203 are respectively securely connected to the two sliders 207b located on the same double-head threaded rod 210. The double-head threaded rod 210 passes through the driving unit fixing plate 201, and a front end of the double-head threaded rod is securely connected to a male coupling 209. In this embodiment, four double-head threaded rods 210 are provided, and can drive the eight driving backbones 203 to perform cooperative pushing or pulling, and accordingly four male couplings 209 are provided.

In the above embodiment, as shown in FIGS. 1 and 5, the distal structural body 101 is externally covered with an envelope 30, a front end of the envelope 30 is fixedly connected to a surgical end effector 40, a rear end of the envelope 30 is securely connected to a rotary sleeve 301 which is rotatably supported on a front end of the driving unit fixing plate 201, the front end of the driving unit fixing plate 201 is further provided with a rotary shaft 302, a pair of gears 303 meshing with each other are securely arranged on the rotary shaft 302 and the rotary sleeve 301, and a front end of the rotary shaft 302 is securely connected to a male coupling 304. By means of driving the rotary shaft 302 to rotate, the rotary sleeve 301 and the envelope 30 can be driven to rotate so as to drive the surgical end effector 40 to rotate, thereby implementing the directional adjustment of the surgical end effector 40 around its own axis.

Figure 8:
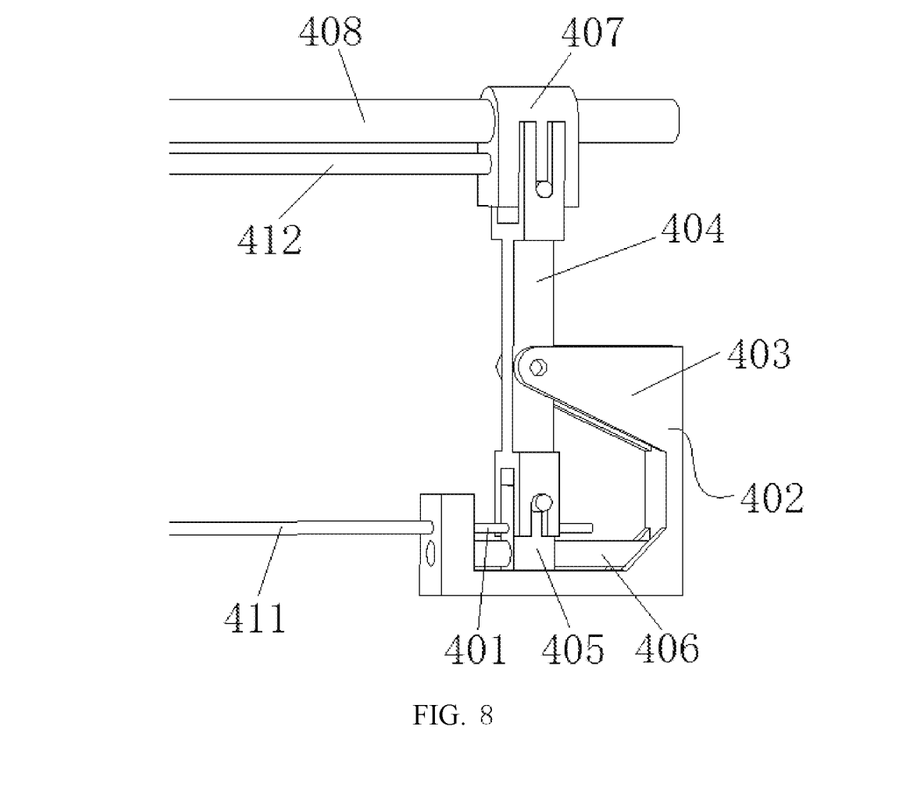
FIG. 8 is a structural schematic diagram of a surgical end effector driving mechanism according to the present invention.

In the above embodiment, as shown in FIGS. 2, 3 and 8, an actuation wire 401 of the surgical end effector 40 passes through the distal structural body 101, the other end of the actuation wire is connected to a surgical end effector driving mechanism 402 located on the channel fixing plate 113, and the surgical end effector driving mechanism 402 controls the surgical end effector 40 (such as surgical forceps) by physically pushing or pulling the actuation wire 401. The actuation wire 401 may also transfer various forms of energy, such as electrical energy and high-frequency vibrations, to achieve specific surgical functions of the surgical end effector 40. The above surgical end effector driving mechanism 402 comprises a base 403 securely connected to the channel fixing plate 113, a connecting rod 404 is rotatably arranged on the base 403, a first slider 405 is connected to one end of the connecting rod 404, the first slider 405 is slidably connected to a first shaft 406 arranged on the base 403, and the actuation wire 401 is securely connected to the first slider 405; and a second slider 407 is connected to the other end of the connecting rod 404, and the second slider 407 is slidably connected to a second shaft 408 arranged on the channel fixing plate 113. A driving threaded rod 409 is rotatably supported on the driving unit fixing plate 201, a front end of the driving threaded rod 409 is provided with a male coupling 410 (as shown in FIG. 5), a third slider (not shown in the figure) is connected to the driving threaded rod 409 by a threaded fit, the third slider is slidably connected to a third shaft (not shown in the figure) located between the driving unit fixing plate 201 and the channel fixing plate 113, and the third slider is securely connected to the second slider 407 by means of a driving rod 412. When the driving threaded rod 409 turns, the third slider will move in a linear motion along the third shaft, while the third slider drives, by means of the driving rod 412 securely connected thereto, the second slider 407 to move in a linear motion along the second shaft 408 so as to drive, by means of the connecting rod 404, the first slider 405 to move in a linear motion along the first shaft 406 so as to physically push or pull the actuation wire 401. Further, a actuation wire guide sleeve 411 is provided between the base 403 and the channel fixing plate 113, and is used to keep the shape of the actuation wire 401 unchanged under a pushing or pulling force.

Figure 9:
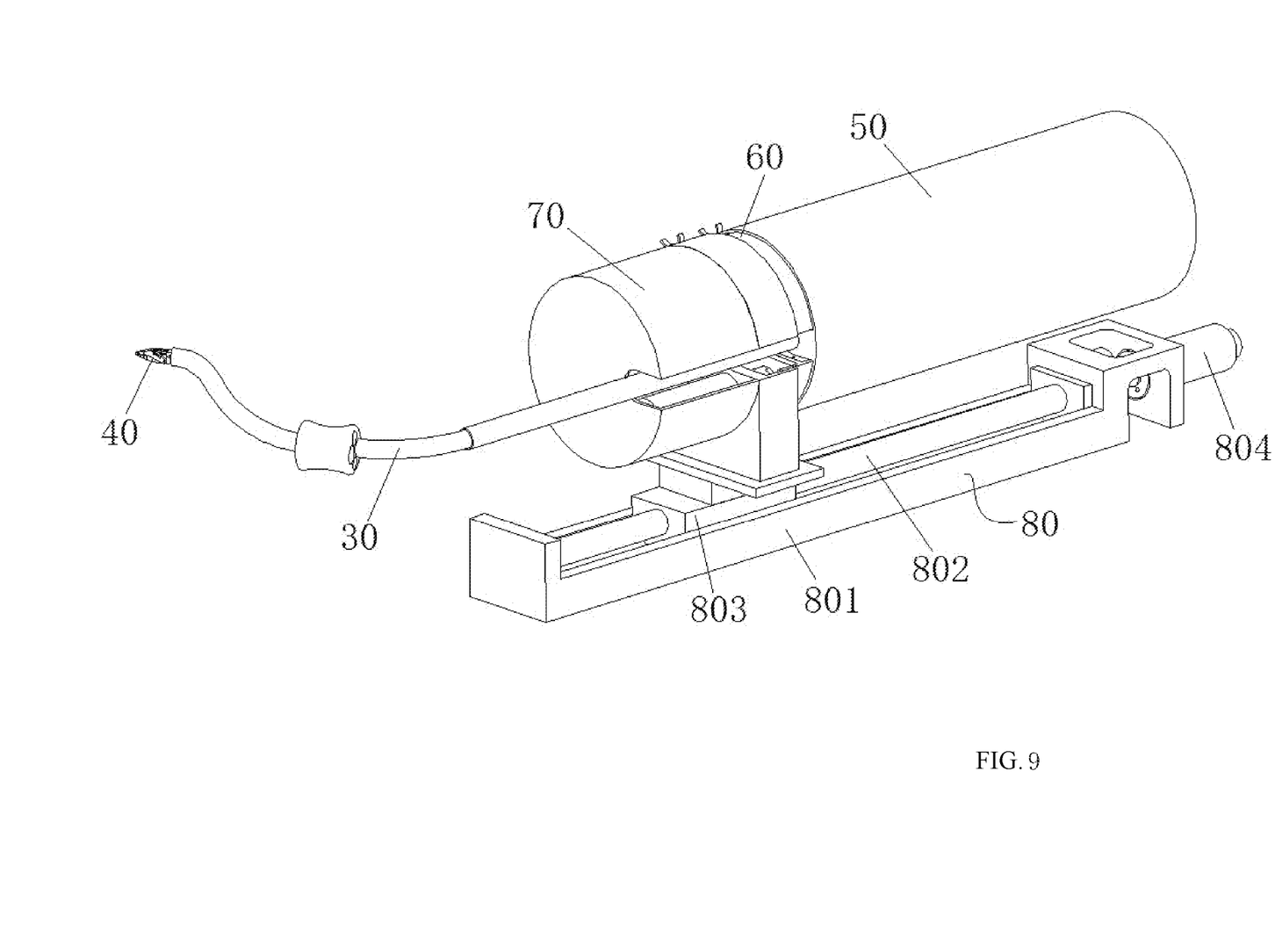
FIG. 9 is a structural schematic diagram according to the present invention with a shell, a sterile barrier, a motor assembly and a linear module being installed.
Figure 10:
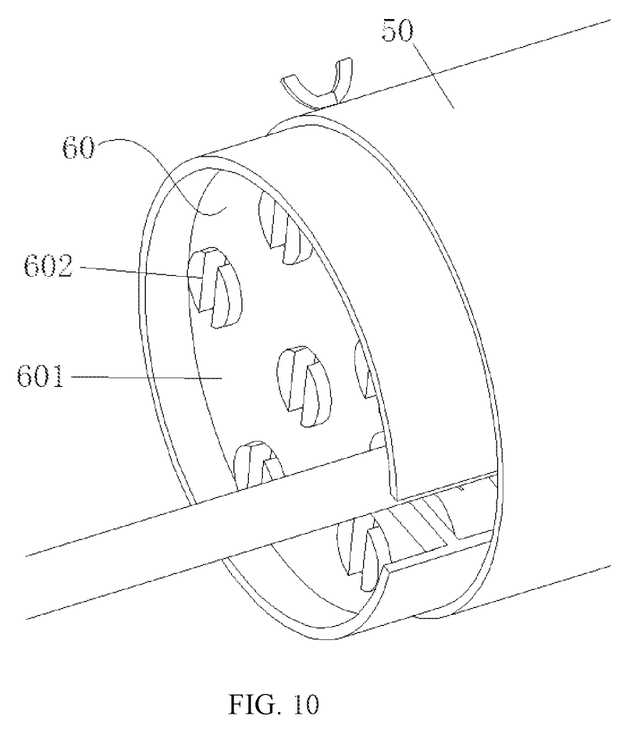
FIG. 10 is a schematic diagram according to the present invention with a sterile barrier being connected to a shell.

In the above embodiment, as shown in FIG. 9, the present invention further comprises a shell 50; and the driving unit fixing plate 201 and the channel fixing plates 113 are all fixedly connected to the shell 50; the proximal structural body 102, the middle connecting body 103 and the driving unit 20 are all located inside the shell 50. A front end of the shell 50 is connected to a motor assembly 70 by means of a sterile barrier 60, as shown in FIG. 10, and the sterile barrier 60 comprises a cover 601 and a female coupling 602 arranged on the cover 601, wherein the cover 601 is respectively connected to the shell 50 and a housing of the motor assembly 70 by means of a fast connection structure, such that the motor assembly 70, the sterile barrier 60 and the shell 50 are detachably connected with each other; and a rear end of the female coupling 602 is connected to the male couplings 209, 304 and 410, and a front end of the female coupling 602 is connected to a motor output shaft in the motor assembly 70 by means of another male coupling (not shown in the figure). A sterile membrane (not shown in the figure) is connected to the periphery of the sterile barrier 60, and is used for separating the unsterilized motor assembly 70 from other sterilized parts, ensuring the clinical practicability of the flexible surgical instrument system.

In the above embodiment, as shown in FIG. 9, the present invention further comprises a linear module 80 (the linear module 80 also being separated from the sterilized parts by means of the sterile membrane) which comprises a support 801 with a sliding groove, wherein a lead screw 802 is rotatably arranged on the support 801, the lead screw 802 is sheathed with a slider 803 which is threadedly fitted with the lead screw 802 and slidably arranged in the sliding groove, one end of the support 801 is provided with a motor 804, and an output shaft of the motor 804 is securely connected to the lead screw 802 by means of a coupling. The housing of the motor assembly 70 is securely connected to the slider 803. When the output shaft of the motor 804 turns, the slider 803 will drive the motor assembly 70, the sterile barrier 60 and the shell 50 to move in a linear motion along the sliding groove, such that the flexible continuous body structure 10 performs a feed motion.

Figure 11:
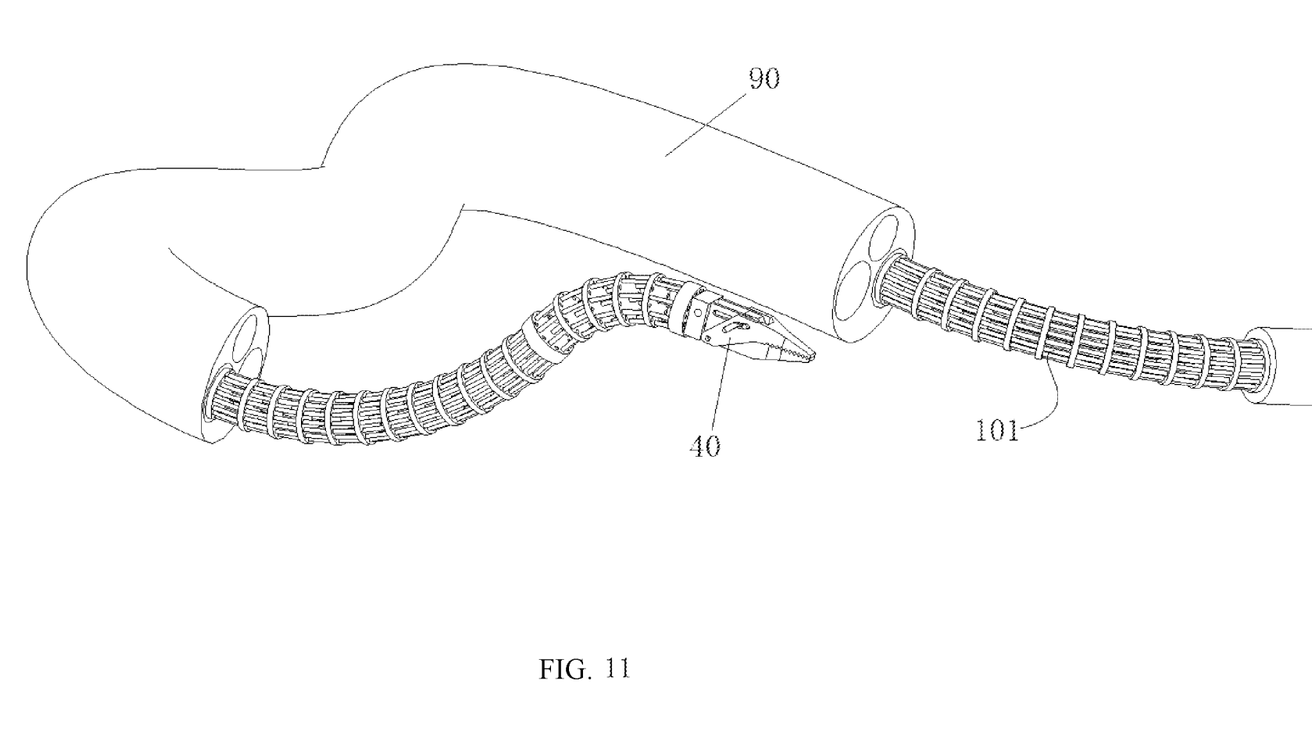
FIG. 11 is a structural schematic diagram of the distal structural body using a flexible sheath according to the present invention.

In the above embodiment, as shown in FIG. 2, in an application, a sheath 90 is fixed at a single incision in the abdominal cavity, and the distal structural body 101, together with the envelope 30 and the surgical end effector 40, can freely pass through a through-hole in the sheath 90 for the passage of the surgical instrument and have access to the surgical site. As shown in FIG. 11, the sheath 90 may also be a flexible sheath that can more easily extend into various natural orifices of the human body and adaptively change shape as the shape of the orifices, one end of the flexible sheath is fixed at the entrance of the orifice, and the distal structural body 101, together with the envelope 30 and the surgical end effector 40, can also freely pass through a through-hole in the flexible sheath for the passage of the surgical instrument and have access to the surgical site.

The present invention has been illustrated only by the above embodiment, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:
1. A flexible surgical instrument, comprising:
  a distal structural body comprising at least one distal structural segment, the at least one distal structural segment comprising a distal fixing disk and distal structural backbones;
  a proximal structural body comprising at least one proximal structural segment, the at least one proximal structural segment comprising a proximal fixing disk, proximal structural backbones, and driving backbones, the distal structural backbones being securely connected in one-to-one correspondence to or the same as corresponding proximal structural backbones, and
  a driving unit comprising a linear motion mechanism operable to convert a first rotary motion into linear motions to cooperatively push or pull a pair of driving backbones of the driving backbones to turn the at least one proximal structural segment;
  a first end of each of the pair of driving backbones is securely connected to the proximal fixing disk; and
  a second end of each of the pair of driving backbones is connected to the linear motion mechanism;
  the linear motion mechanism comprises:
    a first driving slider and a second driving slider;
    a linear motion of the second driving slider is in an opposite direction to a linear motion of the first driving slider;
    second ends of the pair of driving backbones are securely connected to the first driving slider and the second driving slider, respectively;
  the linear motion mechanism further comprises:
    a first threaded rod to receive the first rotary motion;
    a first gear coaxially connected to the first threaded rod;
    a second gear in a meshing with the first gear; and
    a second threaded rod coaxially connected to the second gear;
    the first driving slider in a threaded connection with the first threaded rod; and
    the second driving slider in a threaded connection with the second threaded rod; or the linear motion mechanism further comprises:
a double-head threaded rod to receive the first rotary motion;
the first driving slider and the second driving slider in a threaded connection with two threaded sections of the double-head threaded rod, respectively.

2. The flexible surgical instrument of claim 1, wherein:
proximal ends of the proximal structural backbones are securely connected to the proximal fixing disk; and
distal ends of the distal structural backbones are securely connected to the distal fixing disk.

3. The flexible surgical instrument of claim 1, wherein:
the at least one proximal structural segment further comprises a proximal spacing disk, the proximal structural backbones passing through the proximal spacing disk; and
the at least one distal structural segment further comprises a distal spacing disk, the distal structural backbones passing through the distal spacing disk.

4. The flexible surgical instrument of claim 1, further comprising a middle connecting body comprising:
a first channel fixing plate close to the distal structural body; and
a second channel fixing plate close to the proximal structural body, and
structural backbone guide channels are disposed between the first channel fixing plate and the second channel fixing plate,
the distal structural backbones passing through the structural backbone guide channels.

5. The flexible surgical instrument of claim 4, wherein:
the driving unit comprises:
a driving unit fixing plate disposed at the front of the middle connecting body;
the first threaded rod rotatably is connected to the driving unit fixing plate and the first channel fixing plate; and
the second threaded rod rotatably is connected to the driving unit fixing plate and the first channel fixing plate.

6. The flexible surgical instrument of claim 4, wherein:
the driving unit comprises:
a driving unit fixing plate disposed at the front of the middle connecting body;
the double-head threaded rod rotatably is connected to the driving unit fixing plate and the first channel fixing plate.

7. The flexible surgical instrument of claim 1, further comprising:
a surgical end effector disposed at the distal structural body; and
an actuation wire passing through the distal structural body, the actuation wire comprising a proximal end securely connected to a surgical end effector driving mechanism and a distal end securely connected to the surgical end effector.

8. The flexible surgical instrument of claim 7, further comprising an envelope externally covered in the distal structural body, a distal end of the envelope being securely connected to the surgical end effector to rotate the surgical end effector, and
the driving unit comprises a rotary driving mechanism operable to receive a second rotary motion to rotate the envelope.

9. The flexible surgical instrument of claim 8, wherein the rotary driving mechanism comprises:

a gear set operable to transmit the second rotary motion to the envelope.

10. The flexible surgical instrument of claim 9, wherein the gear set comprises:
a rotary shaft to receive the second rotary motion;
a first driving gear coaxially connected to the rotary shaft;
a second driving gear in meshing with the first driving gear; and
a rotary sleeve coaxially connected to the first driving gear and securely connected to proximal end of the envelope.

11. The flexible surgical instrument of claim 7, wherein:
the surgical end effector driving mechanism comprises:
a base;
a connecting rod rotatably connected to the base;
a third slider connected to a first end of the connecting rod, the proximal end of the actuation wire being securely connected to the third slider; and
a fourth slider connected to a second end of the connecting rod,
the connecting rod being operable to covert a linear motion of the fourth slider into an inverse linear motion of the third slider.

12. The flexible surgical instrument of claim 1, wherein:
the at least one distal structural segment comprises a plurality of distal structural segments or the at least one proximal structural segment comprises a plurality of proximal structural segments,
distal structural backbones of a preceding distal structural segment of the plurality of distal structural segments or proximal structural backbones of a preceding proximal structural segments use elastic elongated tubes, distal structural backbones of a next distal structural segment of the plurality of distal structural segments or proximal structural backbones of a next proximal structural segment of the plurality of proximal structural segments are able to pass through corresponding elastic elongated tubes or distal structural backbones of the next distal structural segment or proximal structural backbones of the next proximal structural segment directly pass through corresponding structural backbone passage holes in distal spacing disks of the preceding distal structural segment or in proximal spacing disks of the preceding proximal structural segment, respectively.

13. A flexible surgical instrument system, comprising:
a flexible surgical instrument comprising:
a distal structural body comprising at least one distal structural segment, the at least one distal structural segment comprising a distal fixing disk and distal structural backbones;
a proximal structural body comprising at least one proximal structural segment, the at least one proximal structural segment comprising a proximal fixing disk, proximal structural backbones, and driving backbones, the distal structural backbones being securely connected in one-to-one correspondence to or the same as corresponding proximal structural backbones, and
a driving unit comprising a linear motion mechanism operable to convert a first rotary motion into linear motions to cooperatively push or pull a pair of driving backbones of the driving backbones to turn the at least one proximal structural segment, a first end of each of the driving backbones is securely connected to the proximal fixing disk, and a second end of each of the driving backbones is connected to the linear motion mechanism; and a motor assembly operable to drive the driving unit;
the linear motion mechanism comprises:
   a first driving slider and a second driving slider;
   a linear motion of the second driving slider is in an opposite direction to a linear motion of the first driving slider;
   second ends of the pair of driving backbones are securely connected to the first driving slider and the second driving slider, respectively;
the linear motion mechanism further comprises:
   a first threaded rod to receive the first rotary motion;
   a first gear coaxially connected to the first threaded rod;
   a second gear in a meshing with the first gear; and
   a second threaded rod coaxially connected to the second gear;
   the first driving slider in a threaded connection with the first threaded rod; and
   the second driving slider in a threaded connection with the second threaded rod; or
the linear motion mechanism further comprises:
   a double-head threaded rod to receive the first rotary motion;
   the first driving slider and the second driving slider in a threaded connection with two threaded sections of the double-head threaded rod, respectively.

14. The flexible surgical instrument system of claim 13, further comprising:
   a shell; and
   a sterile barrier disposed between the shell and the motor assembly.

15. The flexible surgical instrument system of claim 14, wherein the sterile barrier comprises:
   a cover; and
   a coupling rotatably arranged on the cover, and the coupling operable to transmit a rotary motion of the motor assembly to the driving unit.

16. The flexible surgical instrument system of claim 13, further comprising:
   a linear module operable to drive the flexible surgical instrument and the motor assembly to perform another linear motion.

* * * * *